United States Patent [19]

Dahlgren et al.

[11] Patent Number: 5,661,121
[45] Date of Patent: Aug. 26, 1997

[54] 2-PROPYL HEPTANOL ALKOXYLATES AND PROCESS OF CLEANING HARD SURFACES THEREWITH

[75] Inventors: Lennart Dahlgren, Ödsmål; Karin Bergström, Kungälv, both of Sweden

[73] Assignee: Berol Nobel AB, Stenungsund, Sweden

[21] Appl. No.: 436,269

[22] PCT Filed: Nov. 12, 1993

[86] PCT No.: PCT/SE93/00967

§ 371 Date: May 16, 1995

§ 102(e) Date: May 16, 1995

[87] PCT Pub. No.: WO94/11331

PCT Pub. Date: May 26, 1994

[30] Foreign Application Priority Data

Nov. 19, 1992 [SE] Sweden ............... 9203478

[51] Int. Cl.$^6$ ............... C11D 1/72; C11D 1/722; C07C 43/11; C23G 1/24
[52] U.S. Cl. ............... 510/245; 510/241; 510/365; 510/421; 510/506; 568/622; 568/625
[58] Field of Search ............... 252/174.21, DIG. 1; 568/622, 625, 655; 510/506, 241, 245, 365, 421

[56] References Cited

U.S. PATENT DOCUMENTS

| | | | |
|---|---|---|---|
| 2,508,036 | 5/1950 | Kosmin | 568/622 |
| 3,340,309 | 9/1967 | Weipert et al. | 568/625 |
| 3,567,784 | 3/1971 | Tsatsos et al. | 568/625 |
| 3,862,243 | 1/1975 | Bellos | 568/625 |
| 3,983,078 | 9/1976 | Collins | 510/453 |
| 4,340,382 | 7/1982 | Morlino et al. | 8/137 |
| 4,410,447 | 10/1983 | Decker et al. | 252/351 |
| 4,983,185 | 1/1991 | Streicher et al. | 8/436 |

FOREIGN PATENT DOCUMENTS

| | | |
|---|---|---|
| 0046582 | 3/1982 | European Pat. Off. . |
| 2145726 | 4/1985 | United Kingdom . |
| 2194536 | 3/1988 | United Kingdom . |

*Primary Examiner*—Ardith Hertzog
*Attorney, Agent, or Firm*—Spencer & Frank

[57] ABSTRACT

An ethoxylate and a process of cleaning a hard surface with a low foaming detergent includes providing a low foaming detergent composed of the ethoxylate having a general formula which is selected from the group consisting of formula (I):

$$C_5H_{11}CH(C_3H_7)CH_2O(C_2H_4O)_nH$$

and formula (II):

$$C_5H_{11}CH(C_3H_7)CH_2O(C_2H_4O)_p(B)_rH,$$

wherein n is 2–16, p is 1–10, r is 1–6, and B is an alkyleneoxy group having 3–4 carbon atoms; and cleaning the hard surface with the low foaming detergent.

11 Claims, No Drawings

2-PROPYL HEPTANOL ALKOXYLATES AND PROCESS OF CLEANING HARD SURFACES THEREWITH

BACKGROUND OF THE INVENTION

1. Field of the Invention

The present invention relates to the use of an alkoxylate of 2-propyl heptanol in compositions for cleaning hard surfaces. The alkoxylate shows low foaming compared with similar compounds having a hydrophobic group of the same size. The alkoxylate may advantageously be used as a surface-active component in detergent compositions.

2. Description of the Related Art

It has long been known to alkoxylate alcohols for obtaining non-ionic surface-active compounds. These compounds have been used e.g. in detergent compositions because of their wetting and dispersing properties. In a number of applications, alkoxylates of $C_{8-11}$ alcohols have however been found to be too high-foaming and/or not to have the desired detergent power. For example, ethoxylates based on branched $C_8$ alcohols often exhibit acceptable foaming but too low a detergent power, whereas ethoxylates based on straight or branched alcohols having a larger hydrocarbon chain often show an acceptable surface activity but too high foaming. Thus, there is a need for new alkylene oxide adducts with an improved ratio of foaming to detergent power.

SUMMARY OF THE INVENTION

It has now been found alkoxylate based on 2-propyl heptanol is suitable for use as a detergent in compositions for cleaning hard surfaces, since it has good detergent and wetting properties as well as low foaming as compared with other alcohols having substantially the same chain length. In formulations, the alkoxylate also has a desirable thickening effect. In addition, it has been found that the alkoxylate is easily degradable and has a surprisingly low biotoxicity. In tests, no skin-irritant effect has been noted.

The alkoxylate for use according to the invention can be illustrated by the formula $$C_5H_{11}CH(C_3H_7)CH_2O(A)_nH \quad (I)$$

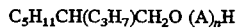

wherein A is an alkyleneoxy group having 2–4 carbon atoms and n is 2–16, preferably 3–12. Preferably, 50–100% of all alkyleneoxy groups are ethyleneoxy groups. In those cases where different alkyleneoxy groups are present in the same compound, they may be added randomly or in block.

Generally, the alkoxylate is an ethoxylate having 3–7, preferably 4–6 ethyleneoxy groups.

In an advantageous mode of execution, ethylene oxide can be added in a first step and thereafter alkylene oxide having 3–4 carbon atoms. These compounds can be illustrated by the formula $$C_5H_{11}CH(C_3H_7)CH_2O(C_2H_4O)_p(B)_rH \quad (II)$$

wherein B is an alkyleneoxy group having 3–4 carbon atoms, p is 1–10 and r is 1–6. Preferably, p is 2–8 and r is 1–4. These compounds have lower foaming than the corresponding compounds without any alkyleneoxy groups having 3–4 carbon atoms.

The alkoxylates for use according to the invention described above can be prepared by adding in a conventional manner in the presence of a conventional alkali catalyst, such as potassium hydroxide or sodium hydroxide, the above-mentioned amounts of alkylene oxide to 2-propyl heptanol, which is a so-called Guebert alcohol. According to a preferred mode of execution, the addition of ethylene oxide is performed using a conventional catalyst which gives a narrower distribution of added ethylene oxide than any alkali catalyst, such as NaOH or KOH. Thus prepared alkoxylates according to the invention have very low foaming. Examples of conventional catalysts giving a narrow distribution of added alkylene oxide are $Ca(OH)_2$, $Ba(OH)_2$, $Sr(OH)_2$ and hydrotalcite. The reaction is preferably conducted in the absence of free water to reduce the amount of by-products and usually at a temperature of 70°–180° C.

The alkoxylate, especially ethoxylate and alkoxylate of formula II, is suitably included in compositions for cleaning hard surfaces, e.g. for degreasing or dishwashing. Especially good results have been obtained when degreasing lacquered or unlacquered metal surfaces. In addition to the alkoxylate, the compositions may also contain other detergents, such as anionic surface-active compounds. Examples hereof are alkyl sulphate, alkyl ether sulphate, alkyl benzene sulphonate, α-olefin sulphonate and alkyl glyceryl sulphonate. Also, the compositions may contain solutising additives, complexing agents and/or pH-adjusting agents, enzymes, other surface-active components, bactericides and perfumes. The compositions are usually aqueous and in the form of emulsions, microemulsions or solutions.

DESCRIPTION OF THE PREFERRED EMBODIMENTS

The invention will be further illustrated by the following Examples.

EXAMPLE 1

Alkoxylates according to the invention are prepared by alkoxylating 2-propyl ethanol with the amounts of alkylene oxide appearing from the Table below in the presence of potassium hydroxide or $Ca(OH)_2$ as catalyst. The resulting products were analysed and structurally determined by gas chromatography and mass spectrometry. The turbidity points were measured in water or monobutylether diethylene glycol. The following results were obtained.

TABLE 1

| Com-pound | Alcohol | Mole of alkylene oxide/mole of alcohol | | Cata-lyst | Turbidity point | |
|---|---|---|---|---|---|---|
| | | | | | Water | BDG |
| 1 | 2-propyl heptanol | 3.0 | EO | KOH | — | 40 |
| 2 | 2-propyl heptanol | 5.5 | EO | KOH | — | 62 |
| 3 | 2-propyl heptanol | 8.4 | EO | KOH | 60 | 73 |
| 4 | 2-propyl heptanol | 3.0 | EO | $Ca(OH)_2$ | — | 29 |
| 5 | 2-propyl heptanol | 5.0 | EO | $Ca(OH)_2$ | — | 52 |
| 6 | 2-propyl heptanol | 7.0 | EO | $Ca(OH)_2$ | — | 61 |
| A | 2-ethyl hexanol | 2 | EO | KOH | — | 28 |
| B | 2-ethyl hexanol | 5 | EO | KOH | 42 | — |
| C | $C_{9-11}$ alcohol[2] | 4 | EO | KOH | — | 62 |
| D | $C_{9-11}$ alcohol[2] | 6 | EO | KOH | 56 | — |
| E | $C_{9-11}$ alcohol[2] | 8 | EO | KOH | 78 | — |
| F | $C_{11}$ alcohol[3] | 3 | EO | KOH | — | 51 |
| G | $C_{11}$ alcohol[3] | 5 | EO | KOH | 27 | — |
| H | $C_{9-11}$ alcohol[2] | 4 | EO | $Ca(OH)_2$ | — | 57 |

EO = ethylene oxide; PO = propylene oxide,
BDG = monobutylether diethylene glycol
[1] PO added first
[2] Dobanol 91 from Shell
[3] Dobanol 1 from Shell

EXAMPLE 2

The foaming properties of the alkoxylates reported in the following Table were measured according to Ross-Miles ASTM D 1173-53. The following results were obtained.

TABLE 2

| Compound | Foam height, cm | |
|---|---|---|
| | 0 min | 5 min |
| 2 | 18 | 7 |
| 4 | 0 | 0 |
| 5 | 5 | 0 |
| 6 | 10 | 5 |
| A | 40 | 10 |
| B | 50 | 0 |
| C | 80 | 20 |
| D | 95 | 30 |
| E | 45 | 15 |
| H | 20 | 5 |

From these results it appears that the compounds according to the invention have lower foaming than the most closely related reference products. Thus, compound 2 has lower foaming than compounds A, B, C, D and E, while compounds 4, 5 and 6 have lower foaming than all the reference compounds.

EXAMPLE 3

On a vertically disposed, lacquered iron plate, smeared with mineral oils, soot, salts and clay was applied 20 ml of a detergent composition made up of the following components.

| Parts by weight | Component |
|---|---|
| 34 | Compound 6 or H |
| 67 | NTA |
| 27 | Ethoxylated quaternary fatty amine |
| 20,000 | Water |

The effect achieved was evaluated both with respect to the area of the cleaned surface (i.e. wettability) and with respect to the cleanness of the cleaned surface. Cleanness was evaluated according to an ascending scale of 1–10, where 1 indicates that no improvement of the cleanness could be observed and 10 indicates a completely clean surface. The following results were obtained.

TABLE 3

| Compound | Cleaned surface, cm | Cleanness |
|---|---|---|
| 6 | 95 | 9 |
| H | 54 | 8 |

From these results it appears that the formulation containing the compound according to the invention yielded both improved cleanness and a larger cleaned area.

EXAMPLE 4

The microtoxicity, which is a measure of the aquatic toxicity, was determined for the compounds below as the water concentration of the compounds at which the ability of luminescent bacteria to emit light for 5 min is reduced by 50%. The following results were obtained.

TABLE 4

| Compound | Concentrate, ppm |
|---|---|
| 2 | 42 |
| 5 | 31 |
| C | 2 |
| D | 3 |
| F | 1 |
| G | 2 |

From these results it appears that the compounds according to the invention have essentially lower microtoxicity than the reference compounds.

What is claimed is:

1. A process of cleaning a hard surface with a low foaming detergent, comprising:

a. providing a low foaming detergent comprised of an alkoxylate having a general formula which is selected from the group consisting of formula (I):

$C_5H_{11}CH(C_3H_7)CH_2O(C_2H_4O)_nH$ and formula (II):

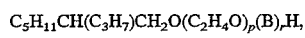

$C_5H_{11}CH(C_3H_7)CH_2O(C_2H_4O)_p(B)_rH,$ wherein n is 2–16, p is 1–10, r is 1–6, and B is an alkyleneoxy group having 3–4 carbon atoms; and b. cleaning the hard surface with the low foaming detergent.

2. The process as defined in claim 1, where n is 3–12.

3. The process as defined in claim 1, where n is 3–7.

4. The process as defined in claim 1, where p is 2–8 and r is 1–4.

5. The process as defined in claim 1, wherein groups $-(C_2H_4O)_n-$ and $-(C_2H_4O)_p-$ in formulae I and II, respectively, are provided by ethoxylating in the presence of an ethoxylation catalyst whereby a distribution range for the alkoxylate is obtained which is narrower than that obtained with NaOH or KOH.

6. The process as defined in claim 1, wherein the hard surface is selected from the group consisting of an unlacquered metal surface and a lacquered metal surface, and wherein cleaning degreases the hard surface.

7. An alkoxylate having a formula:

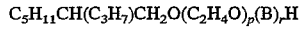

$C_5H_{11}CH(C_3H_7)CH_2O(C_2H_4O)_p(B)_rH$ wherein B is an alkyleneoxy group having 3–4 carbon atoms, p is 1–10, and r is 1–6.

8. The alkoxylate as defined in claim 7, wherein p is 2–8.

9. The alkoxylate as defined in claim 8, where r is 1–4.

10. The alkoxylate as defined in claim 7, where r is 1–4.

11. The alkoxylate defined in claim 7, provided by a process comprising ethoxylation in the presence of an ethoxylation catalyst whereby a distribution range for the alkoxylate is obtained which is narrower than that obtained with NaOH or KOH.

* * * * *